United States Patent [19]
Riego et al.

[11] Patent Number: 6,040,272
[45] Date of Patent: Mar. 21, 2000

[54] AQUEOUS GLYPHOSATE/SURFACTANT COMPOSITIONS FOR BASAL AND DORMANT STEM BRUSH CONTROL

[75] Inventors: Domingo C. Riego, Carmel, Ind.; Kenneth C. Cox, McHenry; Franklin E. Sexton, Richmond, both of Ill.; James C. Meadows, Fernandina Beach, Fla.

[73] Assignee: Monsanto Company, St. Louis, Mo.

[21] Appl. No.: 09/022,599

[22] Filed: Feb. 12, 1998

Related U.S. Application Data

[60] Provisional application No. 60/038,020, Feb. 14, 1997.

[51] Int. Cl.$^7$ .......................... A01N 57/00; A01N 39/02; A01N 37/10; A01N 43/48; A01N 43/40
[52] U.S. Cl. .......................... 504/206; 504/323; 504/324; 504/253; 504/254
[58] Field of Search .................................... 504/116, 206, 504/324, 323, 253, 254

[56] References Cited

U.S. PATENT DOCUMENTS

| | | | |
|---|---|---|---|
| 3,799,758 | 3/1974 | Franz | 71/86 |
| 5,466,659 | 11/1995 | Keeney et al. | 504/130 |
| 5,504,054 | 4/1996 | Murphy | 504/116 |

FOREIGN PATENT DOCUMENTS

| | | | |
|---|---|---|---|
| 1 167 271 | 5/1984 | Canada | A01N 25/30 |
| 1 189 343 | 6/1985 | Canada | A01N 31/14 |
| 0 483 095 | 10/1991 | European Pat. Off. | |
| 0 473 890 | 3/1992 | European Pat. Off. | A01N 43/50 |
| 0 483 095 | 4/1992 | European Pat. Off. | A01N 57/20 |
| WO 89/12394 | 12/1989 | WIPO | A01N 25/30 |

OTHER PUBLICATIONS

Field, Roger J. and Bishop, Nicholas G., "Promotion of Stomatal Infiltration of Glyphosate by an Organosilicone Surfactant Reduces the Critical Rainfall Period," *Pesticide Science*, vol. 24, pp. 55–62, 1988.

Gaskin, Robyn E. and Stevens, Peter J. G., "Antagonism of the Foliar Uptake of Glyphosate into Grasses by Organosilicone Surfactants. Part 1: Effects of Plant Species, Formulation, Concentrations and Timing of Application," *Pesticide Science*, vol. 38, pp. 185–192, 1993.

Gaskin, Robyn E. and Stevens, Peter J. G., "Antagonism of the Foliar Uptake of Glyphosate into Grasses by Organosilicone. Part 2: Effects of Surfactant Structure and Glycerol Addition," *Pesicide Science*, vol. 38, pp. 193–200, 1993.

Stevens, Peter J. G., "Organosilicone Surfactants as Adjuvants for Agrochemicals," *Pesticide Science*, vol. 38, pp. 103–122, 1993.

Stevens, Peter J. G., Gaskin, Robyn E., Hong, Sung–Ok and Zabkiewicz, Jerzy A., "Contributions of Stomatal Infiltration and Cuticular Penetration to Enhancements of Foliar Uptake by Surfactants," *Pesticide Science*, vol. 33, pp. 371–382, 1991.

*Primary Examiner*—Jose' G. Dees
*Assistant Examiner*—Alton Pryor
*Attorney, Agent, or Firm*—Arnold White & Durkee

[57] ABSTRACT

An aqueous herbicidal composition is provided which is useful for controlling woody plants when applied to bark in basal and dormant stem regions of such plants. The composition is an aqueous solution or dispersion of a water-soluble herbicide such as a salt of glyphosate and a surfactant composition, which comprises one or more polyoxyalkylene trisiloxane surfactant(s) and one or more glycols or glycol ethers. Also provided is a method for controlling woody plants comprising applying to bark in basal or dormant stem regions of such plants an aqueous herbicidal composition of the invention.

21 Claims, No Drawings

AQUEOUS GLYPHOSATE/SURFACTANT COMPOSITIONS FOR BASAL AND DORMANT STEM BRUSH CONTROL

This application claims the benefit of U.S. Provisional Patent Application Ser. No. 60/038,020 filed Feb. 14, 1998.

This invention relates to an aqueous herbicidal composition and method for killing or controlling the growth of brush, scrub, arborescent or woody plants such as bushes, shrubs or trees. Herbicides useful herein are water-soluble and do not on their own readily penetrate the bark of dormant woody stems or bark near the base of dormant or non-dormant woody plants. A herbicidal composition of this invention comprises a water-soluble herbicide such as a salt of N-phosphonomethylglycine ("glyphosate"), in aqueous solution with a suitable surfactant composition that provides enhanced effectiveness when applied to bark. Surfactant compositions, without herbicide, are also provided, these being themselves useful as carriers for, or adjuvants to, a water soluble herbicide when that herbicide is applied to bark, or even for applications other than to bark. Described herein are aqueous herbicidal compositions and surfactant compositions found to be useful for this purpose, as well as a method for using these herbicidal and surfactant compositions.

BACKGROUND OF THE INVENTION

Certain water-soluble herbicides (e.g., salts of glyphosate, 2,4-D, dicamba, triclopyr, imazapyr, etc.) are useful for suppressing the growth of or killing unwanted woody plants (trees, shrubs, brush, etc.). These herbicides may be formulated in aqueous media that are effective when applied to foliage, but they tend not to give the desired herbicidal effectiveness when applied to bark, such as on dormant woody stems or near the base of dormant or non-dormant woody plants. It is believed that the failure of these aqueous applications is a product of inadequate penetration of the herbicide through the highly hydrophobic or water-repellent outer layers of the bark.

Through-bark applications are, nevertheless, desired methods of herbicidal treatment. The bark near the base of a woody plant may prove more accessible and readily covered than the foliage of such a plant. Through-bark application also permits control of deciduous woody species during winter or other months of sparse foliage, thereby extending the useful season for herbicidal treatment.

One approach that is prevalent in the art has been to convert the water-soluble herbicide into an oil-soluble form, such as an ester, and apply it to the bark in an oil-based carrier. For example, the herbicide triclopyr has been introduced as the 2-butoxyethyl ester in combination with an oil carrier, sometimes referred to as "basal oil." Attempts have also been made to introduce water-soluble herbicides such as salts in oil-based carriers, or in admixture with oil-based adjuvants. But the physical incompatibility between these ingredients makes it difficult to obtain a homogeneous mixture. Even with emulsifiers, it may be difficult to make a storage stable composition containing a water soluble herbicide and sufficient oil to give the desired herbicidal effectiveness when the herbicidal composition is applied to bark.

Aqueous herbicidal formulations are desirable, both for their ease of handling and for their benign environmental impact (as compared to oil-based formulations). The present invention provides a surfactant composition that permits the use of aqueous herbicidal formulations in woody stem applications. This is accomplished through the use of certain organosilicone surfactants, in combination with glycol or glycol ester (and possibly other) materials.

Water-soluble herbicides, such as glyphosate salts, have typically been formulated with surfactants for foliar application, so that when water is added, the resulting sprayable composition will more easily and effectively cover the foliage (e.g., the leaves or other photosynthesizing organs) of plants. Thus, for example, glyphosate salts have been formulated with surfactants such as polyoxyalkylene-type surfactants including, among other surfactants, polyoxyalkylene alkylamines. Commercial formulations of glyphosate herbicide marketed under the trademark ROUNDUP® have been formulated by Monsanto with such a polyoxyalkylene alkylamine, in particular a polyoxyethylene tallowamine, identified as MON 0818.

It is also known to formulate glyphosate herbicide with polyoxyalkylene polysiloxane surfactants, in particular polyoxyethylene trisiloxane surfactants, such as the commercial organosilicone surfactant Silwet® L-77, available from OSi Specialties, a group of Witco Corporation. Among the numerous studies of the foliar uptake of glyphosate herbicide combined with Silwet® L-77 are those reported by Field & Bishop in *Pesticide Science,* 1988, Vol. 24, pp. 55–62; Stevens et al. in *Pesticide Science,* 1991, Vol. 33, pp. 371–82; Gaskin & Stevens in *Pesticide Science.* 1993, Vol. 38, pp. 185–92; and Gaskin & Stevens in *Pesticide Science,* 1993, Vol. 38, pp. 193–200. An extensive review of 160 references relating to the use of organosilicones as adjuvants for agrochemicals was provided by Stevens in *Pesticide Science,* 1993, Vol. 38, pp. 103–22. In fact, so many studies are reported in this area that OSi Specialties has published a *Bibliography of Silwet® Organosilicone Surfactants As Agricultural Adjuvants* (1996), which is indexed for computer searching. This reference lists hundreds of published studies of commercial organosilicone surfactants in agricultural applications. This bibliography is available to the public through the publisher's office in Tarrytown, N.Y.

In contrast to the vast literature relating to foliar applications of aqueous herbicidal compositions such as those containing glyphosate, information relating to glyphosate application to the basal and dormant stem portions of plants is sketchy. Typically, through-bark, penetration of woody stems has been accomplished by formulating water-insoluble herbicidal materials with oils. In contrast to the oil-based stem treatments of the prior art, a herbicidal composition of the present invention is substantially aqueous or water-miscible or water-soluble, thereby avoiding the expense and environmental impacts of the oil-based systems. The present invention is especially useful in the control of bushy plants such as salt cedar, alder, Brazilian pepper, mesquite, red maple, hickory, and greenbriars. It also permits application of herbicide during winter months, when the species to be controlled may have lost their foliage. It can readily be appreciated that the herbicide uptake behavior for plant stem tissue is dramatically different from that for foliar tissue. Thus different techniques and approaches to enhancement of uptake are warranted. It has been found that the surfactant composition of the present invention is especially useful for this purpose.

SUMMARY OF THE INVENTION

The invention can be described as an aqueous herbicidal composition useful for controlling woody plants when applied to bark, and in particular to bark in basal and dormant stem regions of such plants. More specifically, the herbicidal composition of this invention comprises (a) water, having dissolved or dispersed therein (b) a herbicidally effective amount of a water-soluble herbicide and (c) about 10% to about 90% by weight of a surfactant composition. The surfactant composition comprises:

(i) about 5% to about 35% by weight of one or more polyoxyalkylene trisiloxane surfactant(s) each having a structure corresponding to formula (I):

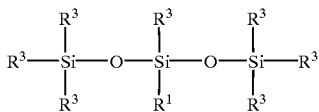

where $R^1$ is —$C_nH_{2n}O(CH_2CH_2O)_a(CH_2CH(CH_3)O)_b$ $R^2$, in which n is 1 to 6, a is 1 to about 30, b is 0 to about 3 and $R^2$ is hydrogen or a $C_{1-4}$ hydrocarbyl or $C_{2-4}$ acyl group, and where $R^3$ groups are independently $C_{1-4}$ hydrocarbyl groups; and (ii) about 50% to about 95% by weight of one or more glycols or glycol ethers each having a structure corresponding to formula (II):

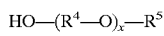

where $R^4$ groups are independently linear or branched $C_{2-6}$ alkylene groups, x is 1 to about 4 and $R^5$ is hydrogen or a $C_{1-4}$ hydrocarbyl group.

The invention can also be described as a method for controlling woody plants comprising a step of applying to bark, and in particular to bark in basal or dormant stem regions of such plants an amount of an aqueous herbicidal composition as just described sufficient to substantially injure or kill the plants.

A preferred water-soluble herbicide for use in a composition or method of the invention is a salt of N-phosphonomethylglycine. As a result of the invention it is now possible to control woody plants effectively with an aqueous composition applied to bark in place of the oil-based compositions previously used for that purpose.

DETAILED DESCRIPTION OF THE INVENTION

The following sets forth in detail the compositions and methods of the present invention, through which good control of woody plants is achieved by basal or dormant stem, or other bark, application of an aqueous herbicidal composition.

Herbicides

The herbicides useful in a composition or method of this invention are water-soluble herbicides and are preferably present at a concentration of about 5% to about 50% by weight of a contemplated composition. Any water-soluble herbicide which has herbicidal activity against woody, brush or arborescent plants can be used, but it is preferred to use a water-soluble salt of N-phosphonomethylglycine (glyphosate), 2,4-dichlorophenoxyacetic acid (2,4-D), dicamba, triclopyr or imazapyr.

The invention is more particularly described with respect to glyphosate and herbicidal derivatives thereof such as salts and other water-soluble compounds which are converted to glyphosate in plant tissues or which otherwise provide glyphosate ion. The term "glyphosate" when used herein is to be understood to encompass such derivatives unless the context requires otherwise.

Illustratively, glyphosate and its salts useful herein are disclosed in U.S. Pat. No. 3,799,758 to Franz, the relevant disclosure of which is incorporated herein by reference. Glyphosate salts that can be used according to this invention include (but are not restricted to) alkali metal, for example sodium and potassium, salts; ammonium salt; $C_{1-16}$ alkylammomium, for example dimethylammonium and isopropylammonium, salts; $C_{1-16}$ alkanolammonium, for example monoethanolamine, salts; $C_{1-16}$ alkylsulfonium, for example trimethylsulfonium, salts; and mixtures thereof. The herbicidal compositions sold by Monsanto Company as ROUNDUP®, ROUNDUP® ULTRA and ACCORD® herbicides contain the monoisopropylammonium (IPA) salt of N-phosphonomethylglycine. The herbicidal compositions sold by Monsanto Company as ROUNDUP® DRY and RIVAL® herbicides contain the ammonium salt of N-phosphonomethylglycine. The herbicidal composition sold by Monsanto Company as ROUNDUP® GEOFORCE herbicide contains the sodium salt of N-phosphonomethylglycine. The herbicidal composition sold by Zeneca Limited as TOUCHDOWN® herbicide contains the trimethylsulfonium salt of N-phosphonomethylglycine. Most of the ammonium, alkylammonium, alkanolammonium, alkylsulfonium and alkali metal salts of glyphosate are highly water-soluble, thereby allowing for highly concentrated solutions that may be diluted at the site of use.

"Herbicidal effectiveness," as used herein, refers to the observable (and desired) degree of control, which is inclusive of the actions of (1) killing, (2) inhibiting growth, reproduction or proliferation, and (3) removing, destroying, or otherwise diminishing the occurrence and activity of plants, and is applicable to any of these actions, or any combinations thereof. The data set forth herein report "control" as a percentage following the standard procedure in the art which reflects a visual assessment of plant mortality and growth reduction by comparison with untreated plants, made by technicians specially trained to make and record such observations. In all cases, a single technician makes all assessments of percent control within any one experiment or trial. Such measurements are relied upon and regularly reported by the Monsanto Company in the course of its herbicide business. Typically, adequate herbicidal effectiveness for commercial use corresponds to about 85% control, but in the brush and woody weed control applications in which the present invention is useful, minimum acceptable control levels are often lower than 85%. Over two decades of glyphosate use and published studies relating to such use have provided abundant information from which a weed control practitioner may select glyphosate application rates that are herbicidally effective on particular species at particular growth stages in particular environmental conditions.

The Surfactant Composition

The surfactant composition of the present invention is selected with several objectives in mind. First, it is believed that previously known aqueous herbicide compositions generally give poor herbicidal effectiveness when applied to bark because the herbicide does not penetrate bark well when applied in such compositions. Therefore, without being bound by theory, it is believed that the surfactant composition of the present invention is able, when applied in a tank mix or in a premixed formulation with the herbicide component, to enhance penetration of the herbicide through the bark of woody trunks and stems. One way to accomplish this is to provide more intimate contact between the applied herbicidal composition and the microtopographically rough surface of the bark, for example by flattening the contact angle of the composition, so as to permit the composition to spread into crevices and pores in the bark. However, other modes of enhancement are also possible. For example, the surfactant composition may also enhance sticking or adhesion to bark when used in aqueous solution, and it may allow the solution to dry on a time scale that is effective to permit penetration. It has been found that a surfactant composition containing certain combinations of a polyoxyalkylene trisiloxane surfactant and one or more glycols, with optional additional ingredients, enhances herbicide uptake—possibly by the route detailed above.

A contemplated herbicidal composition contains about 10% to about 90% by weight and preferably about 25% to about 75% of the selected surfactant composition.

Suitable surfactant compositions can be prepared using polyoxyethylene heptamethyl trisiloxanes, which have the following general formula:

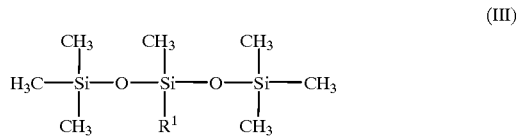
(III)

where $R^1$ is —$C_nH_{2n}O(CH_2CH_2O)_aR^2$, in which n is 3 or 4, a is 1 to about 30 and $R^2$ is hydrogen or a methyl, ethyl or acetyl group. Trisiloxanes of the above formula are generally described in product literature of OSi Specialties, a group of Witco Corporation and in U.S. Pat. No. 3,505,377. Several of such trisiloxanes are ethoxylated organosilicone wetting agents available from OSi Specialties as Silwet® silicone glycol copolymers.

In preferred polyoxyethylene heptamethyl trisiloxanes, n is 3 such that a n-propylene or —$(CH_2)_3$— bridge is present between the middle silicon atom of the trisiloxane group and the polyoxyethylene chain, a is about 5 to about 15 and b is 0. Especially preferred trisiloxanes of this type are those sold commercially in the United States or elsewhere by OSi Specialties as Sukwet® L-77, Silwet® 408 and Silwet® 800, by Dow-Corning as Sylgard® 309, and by Exacto, Inc., as Qwikwet[7]® 100. In the most preferred polyoxyethylene heptamethyl trisiloxanes, $R^2$ is hydrogen.

A contemplated surfactant composition useful in this invention contains about 5% to about 35% by weight, preferably about 5% to about 20% by weight, of the polyoxyalkylene trisiloxane. A blend of more than one polyoxyalkylene trisiloxane can be used, in which case the preferred total amount of all polyoxyalkylene trisiloxanes present in the surfactant composition is as above.

In addition to the polyoxyalkylene trisiloxane, the surfactant composition used in the present invention contains a glycol or glycol ester of formula (II) above. A contemplated surfactant composition contains about 50% to about 95% by weight of the glycol or glycol ester. Preferred glycols and glycol esters include but are not limited to monoethylene glycol, diethylene glycol, propylene glycol or the methyl, ethyl, n-propyl, n-butyl or t-butyl ethers thereof, dipropylene glycol or the methyl, ethyl, n-propyl, n-butyl or t-butyl ethers thereof, tripropylene glycol, or the methyl, ethyl, n-propyl, n-butyl or t-butyl ethers thereof, 1,3-butanediol, 1,4-butanediol, 2-methyl-1,3-propanediol, 2,2-dimethyl-1, 3-propanediol, 2-methyl-1,3-pentanediol and 2-methyl-2,4-pentanediol. More preferred are glycols having 4 or more carbon atoms. Of these, 2-methyl-1,3-propanediol and 1,4-butanediol are the most preferred glycols. A blend or mixture of several glycols may be used, in which case the preferred total amount of all glycols present is as above. In such a case, it is further preferred that at least one of the glycols in the blend be a $C_4$ or higher glycol, especially 2-methyl-1,3-propanediol or 1,4-butanediol. In another preferred embodiment, the surfactant composition contains about 50% to about 80% by weight of 2-methyl-1,3-propanediol, 1,4-butanediol or a mixture thereof and about 5% to about 30% by weight of propylene glycol.

The glycol or glycol ester component brings numerous advantages, including the unexpected advantage that it increases penetration of a herbicidal composition into or through bark. As the glycol or glycol ester component is of substantially lower cost than the polyoxyalkylene trisiloxane component, a mixture composition containing a relatively large amount of the former, for example 75–90% by weight, and a relatively small amount of the latter, example 10–25% by weight, is in most cases much more economical in use than a position consisting entirely of the polyoxyalkylene trisiloxane. Yet a mixture composition as just described has been found to provide effectiveness of a herbicide co-applied to bark at least equal to that provided by the same amount of a polyoxyalkylene trisiloxane alone. Another advantage of a glycol or glycol ester in the present invention is that it lowers the pour point of the composition, which is the minimum temperature at which the composition can readily be poured.

In addition to the polyoxyalkylene trisiloxane and glycol or glycol ester components, a surfactant composition useful in the present invention may include additional ingredients, including other surfactants. It often proves desirable to employ additional surfactants in order, for example, to moderate the spreading properties imparted to the composition by the polyoxyalkylene trisiloxane component. Thus in one embodiment the surfactant composition contains a spread inhibiting amount of about 5% to about 30% by weight of one or more nonionic surfactant(s).

The term "spread inhibiting" as applied to a nonionic surfactant refers to a test that can be conducted on any suitable homogeneous substrate, but herein refers specifically to a test conducted on a substrate of Parafilm® M. A single 10 microliter droplet of a test solution is deposited from a micropipette on to the Parafilm® M substrate and the diameter of spread of the droplet is measured after 30 seconds. Test solutions are prepared at equal polyoxyalkylene trisiloxane concentrations, typically 0.1% by weight. A polyoxyalkylene trisiloxane surfactant and a nonionic surfactant are selected for a test to determine whether or not the nonionic surfactant inhibits the spreading property of the polyoxyalkylene trisiloxane surfactant. Test solution A is prepared containing only the selected polyoxyalkylene trisiloxane surfactant. Test solution B is prepared containing the selected polyoxyalkylene trisiloxane surfactant and the selected nonionic surfactant at a selected weight/weight ratio. If the measured diameter of spread of a droplet of solution B is less than that of a droplet of solution A, it can be concluded that the nonionic surfactant inhibits the spreading property of the polyoxyalkylene trisiloxane surfactant at the weight/weight ratio tested. Such a result is deemed a "positive" result. A "spread inhibiting amount" of a nonionic surfactant in a surfactant composition of the invention is an amount in relation to the amount of polyoxyalkylene trisiloxane present that produces a positive result in the test just described.

For example, the spread diameter of 0.1% by weight of the polyoxyalkylene trisiloxane Qwikwet[7]® 100 in the above test is 8.8 mm. The spread diameter of a mixture of Qwikwet[7]® 100 and the nonionic surfactant Neodol™ 91-6, each at 0.1% by weight, is 7.0 mm. This is a positive result, demonstrating that when Neodol™ 91-6 is present in a surfactant composition at a 1:1 weight/weight ratio with Qwikwet⁷® 100, it is present in a spread inhibiting amount as defined herein.

Preferred nonionic surfactants for inclusion in surfactant compositions useful in the invention are polyoxyethylene (5–30) $C_{8-22}$ alkylethers and polyoxyethylene (5–30) $C_{8-12}$ alkylphenylethers, wherein "(5–30)" means that the average number of ethylene oxide units in the polyoxyethylene chains of these surfactants is from about 5 to about 30. Examples of such nonionic surfactants include polyoxyethylene nonylphenols, octanols, decanols and trimethylnonanols. Particular nonionic surfactants that have proved useful include Neodol™ 91-6 of Shell (a polyoxyethylene (6) $C_{9-11}$ linear primary alcohol), Neodol™ 1-7 of shell (a polyoxyethylene (7) $C_{11}$ linear primary alcohol), Tergitol™ 15-S-9 of Union Carbide (a polyoxyethylene (9) $C_{12-15}$ secondary alcohol) and Surfonic™ NP95 of Huntsman (a polyoxyethylene (9.5) nonylphenol).

Other nonionic surfactants may likewise be found useful, including without restriction polyoxyethylene polyoxypropylene block copolymers and alkyl polyglucosides. Cationic, anionic or amphoteric surfactants may also be included if desired.

Other optional, additional ingredients include pour point depressants (other than the glycols mentioned above). Such pour point depressants include methanol, ethanol, n-propanol, isopropanol, n-butanol, isobutanol, amyl alcohol, methyl amyl alcohol, cyclohexanol, 2-ethylhexanol, furfuryl alcohol, and d-limonene.

In surfactant compositions of the invention, which are intended for mixing with a water soluble herbicide composition, it is preferred that less than 5% by weight of the composition be water. It is especially preferred that there be substantially no water present in the surfactant composition.

While it is important that the herbicidal and surfactant compositions of the invention be based predominantly on water and water-soluble ingredients, the present invention encompasses compositions additionally containing one or more oils, which may be of vegetable origin (such as methylated vegetable oils) or petroleum derived, together with any standard formulation ingredients such as emulsifiers that might be used to stabilize the oil in the aqueous composition.

Application of the Herbicidal Composition

A herbicidal composition of the present invention is applied as an aqueous solution or dispersion. The term "aqueous" as used herein is not intended to exclude the presence of some small amount of nonaqueous solvent, so long as the predominant solvent present, other than the glycol or glycol ester component of the surfactant composition, is water.

The relative amounts of water, herbicide and surfactant composition present in a contemplated aqueous herbicidal composition will vary depending upon many factors including the plant species to be controlled, the method of application, and the rate of application. However, stable aqueous concentrate compositions of the present invention can be made with glyphosate salts at a concentration from about 5% to about 50%, preferably from about 10% to about 30%, with surfactant composition at a concentration of about 10% to about 90%, preferably about 25% to about 75%, and water making up the balance to 100%. These concentrate compositions can be used without dilution, or diluted before application at the site of use.

Aqueous herbicidal compositions of the present invention can be applied to the bark of basal and/or dormant stem portions of the plants to be treated through any of the appropriate methods that are well known to those having skill in the art. Typically, through-bark applications are made on an individual plant (rather than a field) basis, employing backpack sprayers or similar equipment.

EXAMPLES

The following examples are provided for illustrative purposes only and are not intended to limit the scope of the present invention defined by the claims. In these examples, percentage amounts refer to percent by weight unless otherwise noted. In the following examples, experiments were performed using the following (and other) materials:

Surfactant compositions A–D were used as a carrier or adjuvant for ACCORD® and other herbicides applied to the bark of woody stems of brush or arborescent plants in field tests. These surfactant compositions were prepared by mixing the following components in the proportions shown:

| | percent by weight | | | |
| --- | --- | --- | --- | --- |
| | Surfactant composition | | | |
| Component | A | B | C | D |
| Qwikwet ® 100 | 10 | 10 | 10 | 10 |
| 2-methyl-1,3-propanediol | 90 | 65 | 65 | 0 |
| 1,4-butanediol | 0 | 0 | 0 | 65 |
| propylene glycol | 0 | 15 | 15 | 15 |
| Surfonic ™ NP95 | 0 | 10 | 0 | 0 |
| Neodol ™ 1–7 | 0 | 0 | 10 | 10 |

Qwikwet⁷® 100 is a polyoxyethylene heptamethyltrisiloxane of Exacto, Inc. Surfonic™ NP95 is a polyoxyethylene (9.5) nonylphenol of Huntsman. Neodol™ 1-7 is a polyoxyethylene (7) C11 linear primary alcohol of Shell. ACCORD® herbicide is an aqueous concentrate formulation of Monsanto Company containing 41% by weight isopropylammonium salt of glyphosate, or about 30% by weight of N-phosphonomethylglycine acid equivalent.

Application solutions were prepared in the field by mixing ACCORDS herbicide and one of the above surfactant compositions, with mild agitation. Solutions were applied by backpack sprayer using 55° full cone nozzles at a pressure of 138 kPc. For basal treatment of dormant or non-dormant stems, the bark was sprayed from waist or knee height to ground level, applying sufficient solution to wet the bark to the point of run-off. The herbicidal compositions were applied to wild test plants (rather than to test plants cultivated in a controlled environment). The test plants were typically young trees, having a height of 1–3 m and trunk diameter of 1–5 cm.

At various intervals after treatment, all plants in the test were examined by a single practiced technician to evaluate percent control, which is a visual measurement of the effectiveness of the treatment by comparison with untreated plants. The percent control figures reported represent the average control determined for a sample size of 10–15 treated plants, by comparison with untreated plants. A percent control of 0% indicates no effect, and a percent control of 100% indicates that all of the specimens are completely dead.

Example 1

A test was conducted in Minnesota to determine the effectiveness of ACCORD® herbicide as a basal stem treatment using Composition A as a carrier. Application solutions were composed of 50% ACCORD® herbicide and 50% surfactant composition A by volume. Species tested were oak (Quercus sp., QUESS), sumac (Rhus sp., RHUSS) and trembling aspen (*Populus tremuloides,* POPTM). Applications were made in early July and evaluations were made 34, 75, 398 and 727 days after treatment (DAT).

|     | % control |       |       |
| --- | --------- | ----- | ----- |
| DAT | QUESS     | RHUSS | POPTM |
| 34  | 10        | 5     | 100   |
| 75  | 40        | 40    | 100   |
| 398 | 100       | 100   | 100   |
| 727 | 100       | 100   | 100   |

Example 2

A test was conducted in Pennsylvania to determine the effectiveness of ACCORD® herbicide as a basal stem treatment using surfactant composition A as a carrier. As a comparative treatment, ACCORD® herbicide was also applied in a carrier composed of an invert oil emulsion product sold by Waldrum Specialties under the trademark Thinvert R™. Application solutions were composed of 50% ACCORD® herbicide and 50% carrier by volume. Species tested were red maple (*Acer rubrum,* ACRRB), silver maple (*Acer saccharinum,* ACRSA), green ash (*Fraxinus pensylvanica,* FRXPE), pin cherry (*Prunus pensylvanica,* PRNPE) and oak (Quercus sp., QUESS). Applications were made in late August and evaluations were made 42, 336 and 656 days after treatment (DAT). The following table shows results on woody plants having stems up to 8 cm in diameter and up to 5 m in height.

|     | % control |       |       |       |       |
| --- | ----- | ----- | ----- | ----- | ----- |
| DAT | ACRRB | ACRSA | FRXPE | PRMPE | QUESS |
| Carrier: Surfactant composition A ||||||
| 42  | 0     | 10    | 10    | 30    | 0     |
| 336 | 90    | 100   | 100   | 100   | 90    |
| 656 | 100   | 100   | 100   | 100   | 100   |
| Carrier: Thinvert R ™ ||||||
| 42  | 0     | 5     | 10    | 30    | 5     |
| 336 | 100   | 100   | 100   | 100   | 95    |
| 656 | 100   | 100   | 100   | 100   | 98    |

In this test ACCORD® herbicide was as effective when applied in the oil-free surfactant composition A as in the oil-based carrier Thinvert R™. On larger plants (10 cm or greater diameter, 6.5 m or greater height) control with both treatments was poor and inconsistent.

Example 3

A test was conducted in Kentucky to determine the effectiveness of ACCORD® herbicide, and a mixture of ACCORD® and ARSENAL® 2 herbicides, as basal stem treatments using surfactant composition A as a carrier. As comparative treatments, ACCORD® and ACCORD® plus ARSENAL® 2 were also applied in Thinvert R™. ARSENAL® 2 herbicide of American Home Products is a concentrate formulation of the isopropylammonium salt of imazapyr. Also for comparison, ACCORD® herbicide was applied in an oil carrier, Hy-Grade™ 1 of CWC Chemical, as was the triclopyr herbicide GARLON® EC of Dow Chemical. Application solutions were as shown in the table below, all percentages being by volume. Species tested were red maple (*Acer rubnum,* ACRRB), white ash (*Fraxinus americana,* FRXAM), black cherry (*Prunus serotina,* PRNSO), black locust (*Robinia pseudoacacia,* ROBPS), blackberry (Rubus sp., RUBSS), boxelder (*Acer negundo,* ACRNE), elm (Ulmus sp., ULMSS) and tuliptree (*Liriodendron tulipifera,* LIRTU). Applications were made in early to mid April and evaluations were made 55 and 492 days after treatment (DAT). The designation "n.d." indicates an absence of data.

|     | % control |       |       |       |       |       |       |       |
| --- | ----- | ----- | ----- | ----- | ----- | ----- | ----- | ----- |
| DAT | ACRRB | FRXAM | PRNSO | ROBPS | RUBSS | ACRNE | ULMSS | LIRTU |
| ACCORD ® 25%, Surfactant composition A 25%, water 50% |||||||||
| 55  | 95    | 100   | 100   | 100   | n.d.  | n.d.  | n.d.  | n.d.  |
| 492 | 100   | 100   | 100   | 100   | n.d.  | n.d.  | n.d.  | n.d.  |
| ACCORD ® 50%, Surfactant composition A 50% |||||||||
| 55  | 90    | 95    | 95    | 100   | 100   | 95    | n.d.  | n.d.  |
| 492 | 100   | 100   | 100   | 100   | 100   | 100   | n.d.  | n.d.  |
| ACCORD ® 75%, Surfactant composition A 25% |||||||||
| 55  | 100   | 100   | 100   | 100   | 100   | 95    | n.d.  | n.d.  |
| 492 | 100   | 100   | 100   | 100   | 100   | 100   | n.d.  | n.d.  |
| ACCORD ® 5%, Thinvert R ™ 95% |||||||||
| 55  | n.d.  | 70    | n.d.  | 90    | n.d.  | n.d.  | 50    | n.d.  |
| 492 | n.d.  | 60    | n.d.  | 50    | n.d.  | n.d.  | 50    | n.d.  |

-continued

| | | | | % control | | | | |
|---|---|---|---|---|---|---|---|---|
| DAT | ACRRB | FRXAM | PRNSO | ROBPS | RUBSS | ACRNE | ULMSS | LIRTU |
| ACCORD ® 25%, Thinvert R ™ 75% | | | | | | | | |
| 55 | 95 | 95 | 100 | 100 | n.d. | 90 | n.d. | n.d. |
| 492 | 99 | 100 | 100 | 100 | n.d. | 100 | n.d. | n.d. |
| ACCORD ® 50%, Hy-Grade ™1 oil 50% | | | | | | | | |
| 55 | 95 | 95 | 100 | n.d. | n.d. | n.d. | n.d. | n.d. |
| 492 | 100 | 100 | 100 | n.d. | n.d. | n.d. | n.d. | n.d. |
| ACCORD ® 25%, ARSENAL ® 2%, Surfactant composition A 25%, water 48% | | | | | | | | |
| 55 | 95 | 90 | 100 | 100 | n.d. | 90 | n.d. | n.d. |
| 492 | 100 | 100 | 100 | 100 | n.d. | 100 | n.d. | n.d. |
| ACCORD ® 5%, ARSENAL ® 2%, Thinvert R ™ 93% | | | | | | | | |
| 55 | 90 | 95 | n.d. | n.d. | n.d. | 85 | n.d. | 95 |
| 492 | 85 | 90 | n.d. | n.d. | n.d. | 90 | n.d. | 100 |
| ACCORD ® 25%, ARSENAL ® 2%, Thinvert R ™ 73% | | | | | | | | |
| 55 | 90 | 100 | 100 | 100 | n.d. | 95 | n.d. | n.d. |
| 492 | 100 | 100 | 100 | 100 | n.d. | 100 | n.d. | n.d. |
| GARLON ® 25%, Hy-Grade ™1 oil 75% | | | | | | | | |
| 55 | 90 | 90 | 100 | 100 | 100 | 90 | n.d. | n.d. |
| 492 | 80 | 85 | 100 | 100 | 100 | 90 | n.d. | n.d. |

Example 4

A test was conducted in Ohio to determine the effectiveness of ACCORD® herbicide as a basal stem treatment using surfactant composition A as a carrier. As a comparative treatment, ACCORD® herbicide was applied in a 1% by volume solution of the polyoxyethylene heptamethyltrisiloxane surfactant Silwet® L-77. Also for comparison, GARLON® EC was applied in Penevator Basal Oil™ (a product of Exacto, Inc.). Application solutions were as shown in the table below, all percentages being by volume. Species tested were common sassafras (*Sassafras albidum*, SSAAL), red maple (*Acer rubrum*, ACRRB), white ash (*Fraxinus americana*, FRXAM), black cherry (*Prunus serotina*, PRNSO), multiflora rose (*Rosa multiflora*, ROSMU), elm (*Ulmus* sp., ULMSS) and hickory (*Carya* sp., CYASS). Applications were made in early April and evaluations were made 64 and 499 days after treatment (DAT).

| | | | | % control | | | | |
|---|---|---|---|---|---|---|---|---|
| DAT | SSAAL | ACRRB | FRXAM | PRNSO | ROSMU | ULMSS | CYASS | |
| ACCORD ® 25%, Surfactant composition A 75% | | | | | | | | |
| 64 | n.d. | 95 | n.d. | 100 | n.d. | n.d. | 90 | |
| 499 | n.d. | 95 | n.d. | 100 | n.d. | n.d. | 98 | |
| ACCORD ® 50%, Surfactant composition A 50% | | | | | | | | |
| 64 | n.d. | 90 | 90 | 100 | 100 | 90 | 90 | |
| 499 | n.d. | 100 | 100 | 100 | 100 | 98 | 100 | |
| ACCORD ® 75%, Surfactant composition A 25% | | | | | | | | |
| 64 | n.d. | 100 | 95 | 100 | 100 | 90 | 90 | |
| 499 | n.d. | 100 | 100 | 100 | 100 | 100 | 100 | |
| ACCORD ® 50%, Silwet ® L-77 1%, water 49% | | | | | | | | |
| 64 | 80 | 70 | 50 | n.d. | n.d. | n.d. | n.d. | |
| 499 | 75 | 70 | 50 | n.d. | n.d. | n.d. | n.d. | |
| GARLON ® 25%, Penevator Basal Oil ™ 75% | | | | | | | | |
| 64 | 90 | n.d. | 90 | n.d. | n.d. | n.d. | n.d. | |
| 499 | 90 | n.d. | 95 | n.d. | n.d. | n.d. | n.d. | | n.d.: no data

Example 5

A test was conducted in Kentucky to determine the effectiveness of ACCORD® herbicide, and a mixture of ACCORD® and ARSENAL® 2 herbicides, as basal stem treatments using surfactant composition A as a carrier. As comparative treatments, ACCORD® and ACCORD® plus ARSENAL® 2 herbicides were applied in Thinvert R™.

Also for comparison, ADDORD® herbicide was applied in Hy-Grade™ 1 oil. Application solutions were as shown in the table below, all percentages being by volume. Species tested were oak (Quercus sp., QUESS), black locust (*Robinia pseudoacacia*, ROBPS), cedar (Cedrus sp., CEUSS), black cherry (*Prunus serotina*, PRNSO), boxelder (*Acer negundo*, ACRNE), blackberry (Rubus sp., RUBSS), white ash (*Fraxinus americana*, FRXAM), dogwood (Cornus sp., CRWSS), elm (Ulmus sp., ULMSS) and red maple (*Acer rubrum*, ACRRB). Applications were made in early to mid April and evaluation was made 55 days after treatment (DAT). In the tables below "Surf." refers to "Surfactant composition".

| | % control 55 DAT | | | | | | | | | |
|---|---|---|---|---|---|---|---|---|---|---|
| Application solution | QUESS | ROBPS | CEUSS | PRNSO | ACRNE | RUBSS | FRXAM | CRWSS | ULMSS | ACRRB |
| ACCORD ® 25%, Surf. A 75% | 90 | 95 | n.d. | n.d. | n.d. | n.d. | 100 | 100 | n.d. | n.d. |
| ACCORD ® 25%, Surf. A 25%, water 50% | 90 | 95 | n.d. | 95 | 90 | n.d. | 100 | 100 | n.d. | n.d. |
| ACCORD ® 50%, Surf. A 50% | 95 | 100 | n.d. | 100 | 95 | n.d. | 100 | 100 | 90 | 90 |
| ACCORD ® 75%, Surf. A 25% | 95 | 100 | n.d. | 100 | 100 | 100 | 100 | 100 | 100 | 100 |
| ACCORD ® 5%, Thinvert R ™ 95% | 90 | 90 | 40 | n.d. | n.d. | n.d. | n.d. | n.d. | n.d. | n.d. |
| ACCORD ® 50%, Hy-Grade ™1 oil 50% | n.d. | 100 | n.d. | 100 | n.d. | 100 | n.d. | n.d. | n.d. | n.d. |
| ACCORD ® 25%, ARSENAL ® 2%, Surf. A 25%, water 48% | 90 | 100 | n.d. | 100 | 95 | n.d. | 100 | 100 | 90 | 98 |
| ACCORD ® 5%, ARSENAL ® 2%, Thinvert R ™ 93% | n.d. | 95 | n.d. | 95 | 85 | 90 | n.d. | n.d. | n.d. | n.d. | n.d.: no data

Example 6

A test was conducted in Ohio to determine the effectiveness of ACCORD® herbicide as a basal stem treatment using surfactant composition A as a carrier. As comparative treatments, ACCORD® herbicide was applied in Thinvert R™ and in a 1% by volume aqueous solution of the organosilicone surfactant Silwet® L-77. Also for comparison, a mixture of ACCORD® and ARSENAL® 2 herbicides was applied in Thinvert R™, and GARLON® EC was applied in Penevator Basal Oil™. Application solutions were as shown in the table below, all percentages being by volume. Species tested were hickory (Carya sp., CYASS), elm (Ulmus sp., ULMSS), common sassafras (*Sassafras albidum*, SSAAL), white ash (*Fraxinus americana*, FRXA4), red maple (*Acer rubrum*, ACRRB) and black cherry (*Prunus serotina*, PRNSO). Applications were made in early June and evaluations were made 64 and 499 days after treatment (DAT).

| | % control | | | | | |
|---|---|---|---|---|---|---|
| DAT | CYASS | ULMSS | SSAAL | FRXAM | ACRRB | PRNSO |
| ACCORD ® 25%, Surfactant composition A 75% | | | | | | |
| 64 | 90 | 95 | 90 | 85 | 95 | 100 |
| 499 | 95 | 100 | 98 | 90 | 100 | 100 |
| ACCORD ® 50%, Surfactant composition A 50% | | | | | | |
| 64 | 90 | 95 | 90 | 95 | 90 | 100 |
| 499 | 100 | 100 | 100 | 100 | 100 | 100 |
| ACCORD ® 75%, Surfactant composition A 25% | | | | | | |
| 64 | 90 | 100 | 95 | 95 | 95 | 100 |
| 499 | 100 | 100 | 100 | 100 | 100 | 100 |
| ACCORD ® 5%, Thinvert R ™ 95% | | | | | | |
| 64 | 25 | 40 | n.d. | n.d. | n.d. | 80 |
| 499 | 10 | 50 | n.d. | n.d. | n.d. | 50 |
| ACCORD ® 10%, Thinvert R ™ 90% | | | | | | |
| 64 | n.d. | 90 | 90 | 100 | 95 | 90 |
| 499 | n.d. | 90 | 70 | 90 | 80 | 70 |
| ACCORD ® 50%, Silwet ® L-77 1%, water 49% | | | | | | |
| 64 | 50 | n.d. | n.d. | n.d. | 80 | 90 |
| 499 | 60 | n.d. | n.d. | n.d. | 80 | 70 |
| ACCORD ® 5%, ARSENAL ® 1%, Thinvert R ™ 94% | | | | | | |
| 64 | n.d. | 90 | 90 | 100 | 90 | 80 |
| 499 | n.d. | 70 | 50 | 100 | 80 | 50 |
| GARLON ® 25%, Penevator Basal Oil ™ 75% | | | | | | |
| 64 | 80 | 85 | 90 | 90 | 95 | 100 |
| 499 | 85 | 80 | 85 | 90 | 95 | 100 | n.d.: no data

Example 7

A test was conducted in Pennsylvania to determine the effectiveness of ACCORD® herbicide and a mixture of this herbicide with ARSENAL® 2, as basal stem treatments using surfactant composition B as an adjuvant. As comparative treatments, ACCORD® herbicide was applied in Thinvert R™. Also for comparison, GARLON® EC and a GARLON® EC/ARSENAL® 2 mixture were applied in water with 2% by volume Crop Oil Concentrate. Application solutions were as shown in the table below, all percentages being by volume. Species tested were red oak (Quercus sp., QUERS), black cherry (*Prunus serotina*, PRNSO), green ash (*Fraxinus pennsylvanica*, FRXPE), red maple (*Acer rubrum*, ACRRB), and sugar maple (*Acer saccharum*, ACRSC). The test plants were 2-4 m in height. Applications were made in early April and evaluation was made 162 days after treatment (DAT). In the table below "Surf." refers to "Surfactant composition" and "COC" refers to Crop Oil Concentrate.

| Application solution | % control 162 DAT | | | | |
|---|---|---|---|---|---|
| | ACRRB | ACRSC | FRXPB | PRNSU | QUESS |
| ACCORD ® 10%, Surf. B 45%, water 45% | 81 | 92 | 88 | 88 | n.d. |
| ACCORD ® 25%, Surf. B 37.5%, water 37.5% | 87 | 94 | 93 | 98 | n.d. |
| ACCORD ® 50%, Surf. B 25%, water 25% | 100 | 100 | 94 | 100 | n.d. |
| ACCORD ® 10%, ARSENAL ® 1%, Surf. B 44.5%, water 44.5% | 83 | 74 | n.d. | 93 | 57 |
| ACCORD ® 10%, Thinvert R ™ 90% | 23 | 100 | 79 | 37 | n.d. |
| ACCORD ® 25%, Thinvert R ™ 75% | 63 | 60 | 100 | 49 | n.d. |
| ACCORD ® 50%, Thinvert R ™ 50% | 78 | 100 | 100 | 79 | 60 |
| GARLON ® EC 5%, COC 2%, water 93% | 49 | 50 | 68 | 49 | n.d. |
| GARLON ® EC 5%, ARSENAL ® 0.5%, COC 2%, water 92.5% | 44 | 58 | 89 | 34 | 20 | n.d.: no data

ACCORD® herbicide did not mix well with the Thinvert R™ material, and constant agitation was necessary to prevent separation. No such problem was observed with surfactant composition B of the invention.

Example 8

A test was conducted in Pennsylvania to determine the effectiveness of ACCORD® herbicide, a mixture of ACCORD® and STALKER® herbicides, and a mixture of KRENITE® S and STALKER® herbicides, as basal stem treatments using surfactant composition B as an adjuvant. KRENITE® S is a concentrate formulation of fosamine ammonium of DuPont STALKER® is a concentrated formulation of the isopropylammonium salt of imazapyr, available from American Home Products. As comparative treatments, ACCORD® herbicide was applied in Thinvert R™. Also for comparison, GARLON® EC was applied in Penevator Basal Oil™. Application solutions were as shown in the table below, all percentages being by volume. The species tested was tree-of-heaven (*Ailanthus altissima*, AILAL) having a trunk diameter of about 0.6 to 12 cm. Applications were made in mid April and evaluation was made 157 days after treatment (DAT). At least ten trees were sprayed per treatment. In the table below "Surf." refers to "Surfactant composition".

| Application solution | % control 157 DAT |
|---|---|
| ACCORD ® 10%, Surf. B 45%, water 45% | 57 |
| ACCORD ® 25%, Surf. B 37.5%, water 37.5% | 93 |
| ACCORD ® 50%, Surf. B 25%, water 25% | 47 |
| ACCORD ® 50%, STALKER ® 5%, Surf B 22.5%, water 22.5% | 67 |
| KRENITE ® S 50%, STALKER ® 5%, Surf B 22.5%, water 22.5% | 83 |
| ACCORD ® 10%, Thinvert ™ 90% | 70 |
| ACCORD ® 25%, Thinvert ™ 75% | 60 |
| ACCORD ® 50%, Thinvert ™ 50% | 67 |
| GARLON ® EC 20%, Penevator Basal Oil ™ 80% | 100 |

Example 9

A test was conducted in Kentucky to determine the effectiveness of ACCORD® herbicide as basal stem treatments using surfactant composition B as an adjuvant. Also for comparison, ACCORD® herbicide was applied without any surfactant adjuvant. Application solutions were as shown in the table below, all percentages being by volume. The species tested were black locust (*Robinia pseudoacacia*, ROBPS), black cherry (*Prunus serotina*, PRNSO), and common sassafras (*Sassafras albidum*, SSAAL). For the black locust and black cherry, test groups of trees 1–2 m and 4–8 m in height were identified. For sassafras, trees 1–2 m in height were used. Applications were made in mid November and evaluation was made both 181 and 300 days after treatment (DAT).

| | % control | | | | |
|---|---|---|---|---|---|
| DAT | ROBPS 1–2 m | ROBPS 4–8 m | PRNSO 1–2 m | PRNSO 4–8 m | SSAAL 1–2 m |
| ACCORD ® 10%, Surfactant composition B 10%, water 80% | | | | | |
| 181 | 70 | 40 | 65 | 30 | 70 |
| 300 | 50 | 30 | 50 | 30 | 50 |
| ACCORD ® 10%, Surfactant composition B 25%, water 65% | | | | | |
| 181 | 60 | 40 | 60 | 30 | n.d. |
| 300 | 30 | 20 | 50 | 20 | n.d. |
| ACCORD ® 15%, Surfactant composition B 25%, water 60% | | | | | |
| 181 | 90 | 50 | 90 | 40 | 80 |
| 300 | 70 | 60 | 70 | 50 | 70 |
| ACCORD ® 25%, Surfactant composition B 10%, water 65% | | | | | |
| 181 | 98 | 70 | 99 | 70 | 90 |
| 300 | 90 | 70 | 95 | 70 | 80 |
| ACCORD ® 25%, water 75% | | | | | |
| 181 | 40 | 30 | 55 | 40 | 35 |
| 300 | 10 | 10 | 10 | 0 | 20 | n.d.: no data

Control of the 1–2 m trees was generally better than that of the taller trees.

Example 10

A test was conducted in Pennsylvania to determine the effectiveness of ACCORD® herbicide as basal stem treatments using surfactant composition B as a carrier. Also for comparison, ACCORD® herbicide was applied with Thinvert R™ as a carrier, and GARLON® EC was applied with Hy-Grade™ 1 oil as a carrier. Application solutions were as shown in the table below, all percentages being by volume. The species tested were black locust (*Robinia pseudoacacia*, ROBPS) and black cherry (*Prunus serotina*, PRNSO). The trees tested were 4–8 m in height. Applications were made in mid April and evaluation was made 168 days after treatment (DAT).

| | % control 168 DAT | |
|---|---|---|
| Application solution | ROBPS | PRNSO |
| ACCORD ® 10%, Surfactant composition B 90% | 100 | 100 |
| ACCORD ® 25%, Surfactant composition B 75% | 67 | 100 |
| ACCORD ® 50%, Surfactant composition B 50% | 100 | 100 |
| ACCORD ® 10%, Thinvert R ™ 90% | 0 | 67 |
| ACCORD ® 25%, Thinvert R ™ 75% | 65 | 100 |
| ACCORD ® 50%, Thinvert R ™ 50% | 0 | 100 |
| Garlon EC 20%, Hy-Ggrade ™ 1 oil 80% | 100 | 100 |

Example 11

A test was conducted in Ohio to determine the effectiveness of ACCORD® herbicide as basal stem treatments using surfactant compositions B, C and D as adjuvants. Also for comparison, ACCORD® herbicide was applied with Silkin™ and Silwet® L-77 as adjuvants. Silwet® L-77 is an organisilicone surfactant products of Osi Specialties, a division of Witco Corporation. Silkin™ is an organosilicone surfactant of Terra. Application solutions were as shown in the table below, all percentages being by volume. The species tested were black locust (*Robinia pseudoacacia*, ROBPS), black cherry (*Prunus serotina*, PRNSO), common sassafras (*Sassafras albidum*, SSAAL), and oak (Quercus sp., QUESS). For black locust and black cherry, test groups of trees 1–2 m and 4–8 m in height were identified. For sassafras, trees 1–2 m in height were used. For oak, trees 2–4 m in height were used. Applications were made in mid May and evaluation was made 118 days after treatment (DAT). In the table below "Surf." refers to "Surfactant composition".

| Application solution | % control 118 DAT | | | | | |
|---|---|---|---|---|---|---|
| | ROBPS 1–2 m | ROBPS 4–8 m | PRNSO 1–2 m | PRNSO 4–8 m | FRXPE 2–4 m | SSAAL 1–2 m |
| ACCORD ® 50%, Surf. B 10%, water 40% | 99 | n.d. | 100 | n.d. | 90 | n.d. |
| ACCORD ® 50%, Surf. C 10%, water 40% | 90 | 40 | 100 | 50 | 90 | 90 |
| ACCORD ® 50%, Surf. D 10%, water 40% | 60 | 30 | n.d. | 30 | n.d. | n.d. |
| ACCORD ® 50%, Silkin ™ 10%, water 40% | 70 | 10 | 30 | 10 | 30 | 0 |
| ACCORD ® 50%, Silwet ® L-77 10%, water 40% | 90 | 50 | 95 | 40 | 80 | 70 |

Example 12

A test was conducted in Minnesota to determine the effectiveness of ACCORD® herbicide as basal stem treatments using surfactant compositions B and C as adjuvants. Also for comparison, ACCORD® herbicide was applied with Silkin™. Application solutions were as shown in the table below, all percentages being by volume. The species tested were red maple (*Acer rubrum*, ACRRB) and willow (*Salix sp.*, SAXSS). The maple trees were 4–8 m in height; the willow trees were 2–4 m. Applications were made in late April and evaluation was made 16 days after treatment (DAT).

| Application solution | % control 16 DAT | |
|---|---|---|
| | ACRRB | SAXSS |
| ACCORD ® 50%, Surfactant composition B 10%, water 40% | 75 | 80 |
| ACCORD ® 50%, Surfactant composition C 10%, water 40% | 80 | 85 |
| ACCORD ® 50%, Silkin ™ 10%, water 40% | 50 | 60 |

The present invention may also be embodied in specific modes other than those set forth in the foregoing specification, without departing from the spirit or essential attributes of the invention. Accordingly, reference should be made to the appended claims, rather than the foregoing specification or examples, as indicating the scope of the invention.

What is claimed is:

1. An aqueous herbicidal composition useful for controlling woody plants when applied to bark, comprising:
   a) water, having dissolved or dispersed therein:
   b) a herbicidally effective amount of a water-soluble herbicide; and
   c) about 10% to about 90% by weight of a surfactant composition that comprises:
      i) about 5% to about 35% by weight of one or more polyoxyalkylene trisiloxane surfactant(s) having a structure corresponding to formula (I):

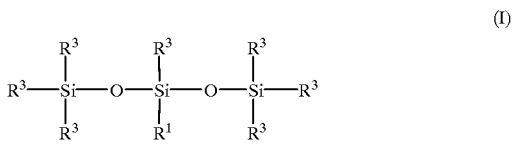

(I)

where $R^1$ is $-C_nH_{2n}O(CH_2CH_2O)_a(CH_2CH(CH_3)O)_bR^2$, in which n is 1 to 6, a is 1 to about 30, b is 0 to about 3 and R is hydrogen or a $C_{1-4}$ hydrocarbyl or $C_{2-4}$ acyl group, and where $R^3$ groups are independently $C_{1-4}$ hydrocarbyl groups; and
      ii) about 50% to about 95% by weight of one or more glycols or glycol ethers having a structure corresponding to formula (II):

(II)

where $R^4$ groups are independently linear or branched $C_{2-6}$ alkylene groups, x is 1 to about 4 and $R^5$ is hydrogen or a $C_{1-4}$ hydrocarbyl group.

2. The herbicidal composition of claim 1, wherein said water-soluble herbicide is present at a concentration of about 5% to about 50% by weight of said herbicidal composition.

3. The herbicidal composition of claim 1, wherein the water-soluble herbicide is a salt of N-phosphonomethylglycine, 2,4-dichlorophenoxyacetic acid, dicamba, triclopyr or imazapyr.

4. The herbicidal composition of claim 1, wherein the water-soluble herbicide is an alkali metal, ammonium, $C_{1-16}$ alkylammonium, $C_{1-16}$ alkanolammonium or $C_{1-16}$ alkylsulfonium salt of N-phosphonomethylglycine.

5. The herbicidal composition of claim 4, wherein, in the formula (I) for said polyoxyalkylene trisiloxane surfactant(s), n is 3 or 4, a is 1 to about 30, b is 0, $R^2$ is hydrogen or a methyl, ethyl or acetyl group and $R^3$ groups are methyl groups.

6. The herbicidal composition of claim 5, wherein, in the formula (II) for said polyoxyalkylene trisiloxane surfactant(s), x is 3.

7. The herbicidal composition of claim 4, wherein the glycol(s) or glycol ether(s) are selected from the group consisting of monoethylene glycol, diethylene glycol, propylene glycol and the methyl, ethyl, n-propyl, n-butyl and t-butyl ethers thereof, dipropylene glycol and the methyl, ethyl, n-propyl, n-butyl and t-butyl ethers thereof, tripropylene glycol and the methyl, ethyl, n-propyl, n-butyl and t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol.

8. The herbicidal composition of claim 4, wherein the glycol(s) or glycol ether(s) each have 4 to 20 carbon atoms.

9. An aqueous herbicidal composition useful for controlling woody plants when applied to bark, comprising:
   a) water, having dissolved or dispersed therein:
   b) about 5% to about 50% of an alkali metal, ammonium, $C_{1-16}$ alkylammonium, $C_{1-16}$ alkanolammonium or $C_{1-16}$ alkylsulfonium salt of N-phosphonomethylglycine; and
   c) a surfactant composition that comprises:
      i) about 5% to about 35% by weight of one or more polyoxyalkylene trisiloxane surfactants having a structure corresponding to formula (III):

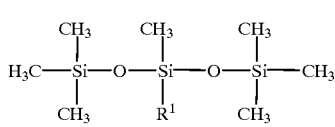

(III)

where $R^1$ is $-(CH_2)_3O(CH_2CH_2O)_aR^2$, in which a is about 5 to about 15 and $R^2$ is hydrogen or a methyl, ethyl or acetyl group; and
      ii) about 50% to about 95% by weight of 2-methyl-1,3-propanediol or 1,4-butanediol or a mixture thereof.

10. The herbicidal composition of claim 9 wherein the amount of 2-methyl-1,3-propanediol, 1,4-butanediol or a mixture thereof is about 50% to about 80% by weight of said surfactant composition and said surfactant composition further comprises one or both of:
      iii) a spread inhibiting amount of about 5% to about 30% by weight of one or more nonionic surfactant(s) selected from polyoxyethylene (5–30) $C_{8-22}$ alkylethers and polyoxyethylene (5–30) $C_{8-12}$ alkylphenylethers; and
      iv) about 5% to about 30% by weight of propylene glycol.

11. A method for killing or controlling a woody plant comprising the step of applying to bark of a basal or dormant stem region of said plant a herbicidal composition comprising:
   a) water, having dissolved or dispersed therein:
   b) a herbicidally effective amount of a water-soluble herbicide; and
   c) about 10% to about 90% by weight of a surfactant composition that comprises:
      i) about 5% to about 35% by weight of one or more polyoxyalkylene trisiloxane surfactant(s) having a structure corresponding to formula (I):

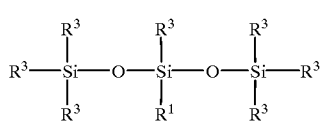

(I)

where $R^1$ is $-C_nH_{2n}O(CH_2CH_2O)_a(CH_2CH(CH_3)O)_bR^2$, in which n is 1 to 6, a is 1 to about 30, b is 0 to about 3 and $R^2$ is hydrogen or a $C_{1-4}$ hydrocarbyl or $C_{2-4}$ acyl group, and where $R^3$ groups are independently $C_{1-4}$ hydrocarbyl groups; and
      ii) about 50% to about 95% by weight of one or more glycols or glycol ethers having a structure corresponding to formula (II):

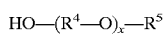

(II)

where $R^4$ groups are independently linear or branched $C_{2-6}$ alkylene groups, x is 1 to about 4 and $R^5$ is hydrogen or a $C_{1-4}$ hydrocarbyl group.

12. The method of claim 11, wherein said water-soluble herbicide is present at a concentration of about 5% to about 50% by weight of said herbicidal composition.

13. The method of claim 11, wherein the water-soluble herbicide is a salt of N-phosphonomethylglycine, 2,4-dichlorophenoxyacetic acid, dicamba, triclopyr or imazapyr.

14. The method of claim 11, wherein the water-soluble herbicide is an alkali metal, ammonium, $C_{1-16}$ alkylammonium, $C_{1-16}$ alkanolammonium or $C_{1-16}$ alkylsulfonium salt of N-phosphonomethylglycine.

15. The method of claim 14, wherein, in the formula (I) for said polyoxyalkylene trisiloxane surfactant(s), n is 3 or 4, a is 1 to about 30, b is 0, $R^2$ is hydrogen or a methyl, ethyl or acetyl group and $R^3$ groups are methyl groups.

16. The method of claim 15, wherein, in the formula (II) for said polyoxyalkylene trisiloxane surfactant(s), x is 3.

17. The method of claim 14, wherein the glycol(s) or glycol ether(s) are selected from the group consisting of monoethylene glycol, diethylene glycol, propylene glycol and the methyl, ethyl, n-propyl, n-butyl and t-butyl ethers thereof, dipropylene glycol and the methyl, ethyl, n-propyl, n-butyl and t-butyl ethers thereof, tripropylene glycol and the methyl, ethyl, n-propyl, n-butyl and t-butyl ethers thereof, 1,3-butanediol, 1,4-butanediol, 2-methyl-1,3-propanediol, 2,2-dimethyl-1,3-propanediol, 2-methyl-1,3-pentanediol and 2-methyl-2,4-pentanediol.

18. The method of claim 14, wherein the glycol(s) or glycol ether(s) each have 4 to 20 carbon atoms.

19. A method for killing or controlling a woody plant comprising the step of applying to bark of a basal or dormant stem region of said plant a herbicidal composition comprising:
   a) water, having dissolved or dispersed therein:
   b) about 5% to about 50% of an alkali metal, ammonium, $C_{1-16}$ alkylammonium, $C_{1-16}$ alkanolammonium or $C_{1-16}$ alkylsulfonium salt of N-phosphonomethylglycine; and
   c) a surfactant composition that comprises:
      i) about 5% to about 35% by weight of one or more polyoxyalkylene trisiloxane surfactants having a structure corresponding to formula (III):

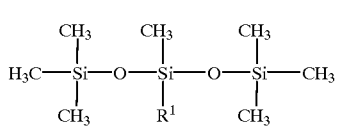

(III)

where $R^1$ is $-(CH_2)_3O(CH_2CH_2O)_aR^2$, in which a is about 5 to about 15 and $R^2$ is hydrogen or a methyl, ethyl or acetyl group; and
      ii) about 50% to about 95% by weight of 2-methyl-1,3-propanediol or 1,4-butanediol or a mixture thereof.

20. The method of claim 19 wherein the amount of 2-methyl-1,3-propanediol, 1,4-butanediol or a mixture thereof is about 50% to about 80% by weight of said surfactant composition and said surfactant composition further comprises one or both of:
      iii) a spread inhibiting amount of about 5% to about 30% by weight of one or more nonionic surfactant(s) selected from polyoxyethylene (5–30) $C_{8-22}$ alkylethers and polyoxyethylene (5–30) $C_{8-12}$ alkylphenylethers; and
      iv) about 5% to about 30% by weight of said surfactant composition of propylene glycol.

21. The method of claim 20, wherein said woody plant is of a species selected from the group consisting of common sassafras (*Sassafras albidum*), red maple (*Acer rubrum*), white ash (*Fraxinus americana*), black cherry (*Prunus serotina*), multiflora rose (*Rosa multiflora*), elm (Ulmus spp.), hickory (Carya spp.), oak (Quercus spp.), sumac (Rhus spp.), trembling aspen (*Populus tremuloides*), silver maple (*Acer saccharinum*), green ash (*Fraxinus pensylvanica*), pin cherry (*Prunus pensylvanica*), blackberry (Rubus spp.), boxelder (*Acer negundo*), tuliptree (*Liriodendron tulipifera*), cedar (Cedrus spp.), dogwood (Cornus spp.), sugar maple (*Acer saccharum*), tree of heaven (*Ailanthus altissima*), and willow (Salix spp.).

\* \* \* \* \*

UNITED STATES PATENT AND TRADEMARK OFFICE
CERTIFICATE OF CORRECTION

PATENT NO. : 6,040,272

DATED : March 21, 2000

INVENTOR(S) : Domingo C. Riego, Kenneth C. Cox, Franklin E. Sexton, James C. Meadows It is certified that error appears in the above-identified patent and that said Letters Patent is hereby corrected as shown below:

In the Claims:

Claim 1, line 27, delete "R" and insert thereof --$R^2$--.

Signed and Sealed this

Twenty-seventh Day of February, 2001

Attest:

NICHOLAS P. GODICI

*Attesting Officer*     *Acting Director of the United States Patent and Trademark Office*